(12) United States Patent
Koretz

(10) Patent No.: US 7,070,276 B2
(45) Date of Patent: Jul. 4, 2006

(54) APPARATUS AND METHOD FOR ACCOMMODATIVE STIMULATION OF AN EYE AND SIMULTANEOUS IPSILATERAL ACCOMMODATIVE IMAGING

(75) Inventor: Jane F. Koretz, Slingerlands, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 25 days.

(21) Appl. No.: 10/727,734

(22) Filed: Dec. 4, 2003

(65) Prior Publication Data

US 2005/0122474 A1 Jun. 9, 2005

(51) Int. Cl.
*A61B 3/14* (2006.01)
*A61B 3/10* (2006.01)

(52) U.S. Cl. ............... 351/206; 351/211; 351/216; 351/221; 351/246; 396/18

(58) Field of Classification Search ............... 351/203, 351/205, 206, 211, 213–216, 221, 237, 243, 351/246, 200; 396/18; 600/558; 606/4–6, 606/10; 601/37
See application file for complete search history.

(56) References Cited

U.S. PATENT DOCUMENTS

| | | | |
|---|---|---|---|
| 4,019,813 A | | 4/1977 | Cornsweet et al. |
| 4,171,877 A | | 10/1979 | Karasawa et al. |
| 4,523,821 A | | 6/1985 | Lang et al. |
| 4,533,221 A | * | 8/1985 | Trachtman .................. 351/203 |
| 4,711,541 A | * | 12/1987 | Yoshino et al. ............. 351/214 |
| 4,778,268 A | * | 10/1988 | Randle ....................... 351/203 |
| 4,863,261 A | | 9/1989 | Flammer |
| 5,139,022 A | * | 8/1992 | Lempert .................... 351/206 |
| 5,208,619 A | | 5/1993 | Campbell |
| 5,237,351 A | * | 8/1993 | Kohayakawa et al. ...... 351/243 |
| 5,309,186 A | * | 5/1994 | Mizuno ...................... 351/212 |
| 5,321,445 A | * | 6/1994 | Fossetti ...................... 351/203 |
| 5,512,965 A | | 4/1996 | Snook |
| 5,757,462 A | * | 5/1998 | Nanjo ........................ 351/206 |
| 5,777,719 A | | 7/1998 | Williams |
| 5,864,382 A | * | 1/1999 | Soya et al. .................. 351/206 |
| 5,870,167 A | * | 2/1999 | Knopp et al. ............... 351/212 |
| 6,286,958 B1 | | 9/2001 | Koest |
| 6,382,795 B1 | | 5/2002 | Lai |
| 6,419,671 B1 | * | 7/2002 | Lemberg ....................... 606/5 |
| 6,575,572 B1 | | 6/2003 | Lai et al. |

(Continued)

FOREIGN PATENT DOCUMENTS

DE 10154194 A1 * 5/2003

*Primary Examiner*—Patricia Bianco
*Assistant Examiner*—John R. Sanders
(74) *Attorney, Agent, or Firm*—Sander Rabin

(57) ABSTRACT

An apparatus comprising an accommodative stimulation device, an electromagnetic wave exposure device, and an imaging device. The apparatus acquires imaging information about an eye by means of the electromagnetic wave exposure device and the imaging device as the apparatus simultaneously stimulates the eye to undergo at least one reversible accommodative transition from any first state of accommodation to any second state of accommodation by means of the accommodative stimulation device. The accommodative stimulation device has an axis of projection that is substantially perpendicular to a visual axis of the eye, along which axis of projection an adjustable accommodative target is projected through a system of Badal optics, having a Badal optical axis coincident with the axis of projection, to strike a half-silvered mirror lying in a plane that forms an angle of about 45 degrees with the axis of projection and the visual axis of the eye.

14 Claims, 10 Drawing Sheets

U.S. PATENT DOCUMENTS

| | | |
|---|---|---|
| 6,739,722 B1 * | 5/2004 | Laguette et al. ............. 351/243 |
| 2003/0012412 A1 * | 1/2003 | Torii et al. .................. 382/117 |
| 2003/0063257 A1 * | 4/2003 | Molebny .................... 351/212 |
| 2003/0063258 A1 * | 4/2003 | Torii et al. .................. 351/214 |
| 2003/0086063 A1 * | 5/2003 | Williams et al. ............. 351/221 |
| 2004/0218142 A1 * | 11/2004 | Wakil et al. ................. 351/205 |
| 2005/0041206 A1 * | 2/2005 | Vogelsang et al. .......... 351/200 |
| 2005/0057722 A1 * | 3/2005 | Koest ......................... 351/205 |

\* cited by examiner

US 7,070,276 B2

APPARATUS AND METHOD FOR ACCOMMODATIVE STIMULATION OF AN EYE AND SIMULTANEOUS IPSILATERAL ACCOMMODATIVE IMAGING

BACKGROUND OF THE INVENTION

1. Technical Field

The present invention pertains generally to the field of visual accommodation, presbyopia and cataractogenesis, and, more particularly, to the acquisition of imaging information about an eye as it is simultaneously stimulated to undergo reversible changes of accommodative state.

2. Related Art

The crystalline lenses of the eyes undergo mechanical, physiological, morphological and refractive changes to adjust the total refractive power of the eyes to maintain sharp visual acuity whenever an object of regard is moved toward and away from the distance at which humans typically view reading material. The aggregate changes experienced by the crystalline lenses of the eyes to maintain sharp visual acuity is referred to as accommodation. At any given time the crystalline lenses and the eyes may be regarded as being in a state of accommodation. In transitioning from one stationary state of accommodation to another stationary state of accommodation, the crystalline lenses undergo a time-dependent process of dynamic accommodation. Heretofore, all attempts to acquire imaging information regarding dynamic accommodation have been unsuccessful, and imaging information has only been acquired regarding the stationary states of accommodation between which dynamic accommodation is operative.

SUMMARY OF THE INVENTION

The present invention is an apparatus comprising an accommodative stimulation device, an electromagnetic wave exposure device, and an imaging device, said apparatus acquiring imaging information about an eye by means of said electromagnetic wave exposure device and said imaging device, as said accommodative stimulation device simultaneously stimulates said eye to undergo at least one reversible accommodative transition from any first state of accommodation to any second state of accommodation, said accommodative stimulation device having an axis of projection that is substantially perpendicular to a visual axis of said eye, along which axis of projection an adjustable accommodative target is projected through a system of Badal optics, having a Badal optical axis coincident with said axis of projection, to strike a half-silvered mirror lying in a plane that forms an angle of about 45 degrees with said axis of projection and said visual axis of said eye.

The present invention advantageously overcomes limitations on the imaging of dynamic accommodation in the art of optics and ophthalmology by providing a technology that effectively "unconceals" dynamic accommodation, thereby lifting limitations that have confined knowledge of accommodation to the static endpoints of the dynamic accommodative process.

DETAILED DESCRIPTION OF THE INVENTION

The detailed description refers to drawings in which like parts are designated by like numerals in the various views.

Figure 1A:
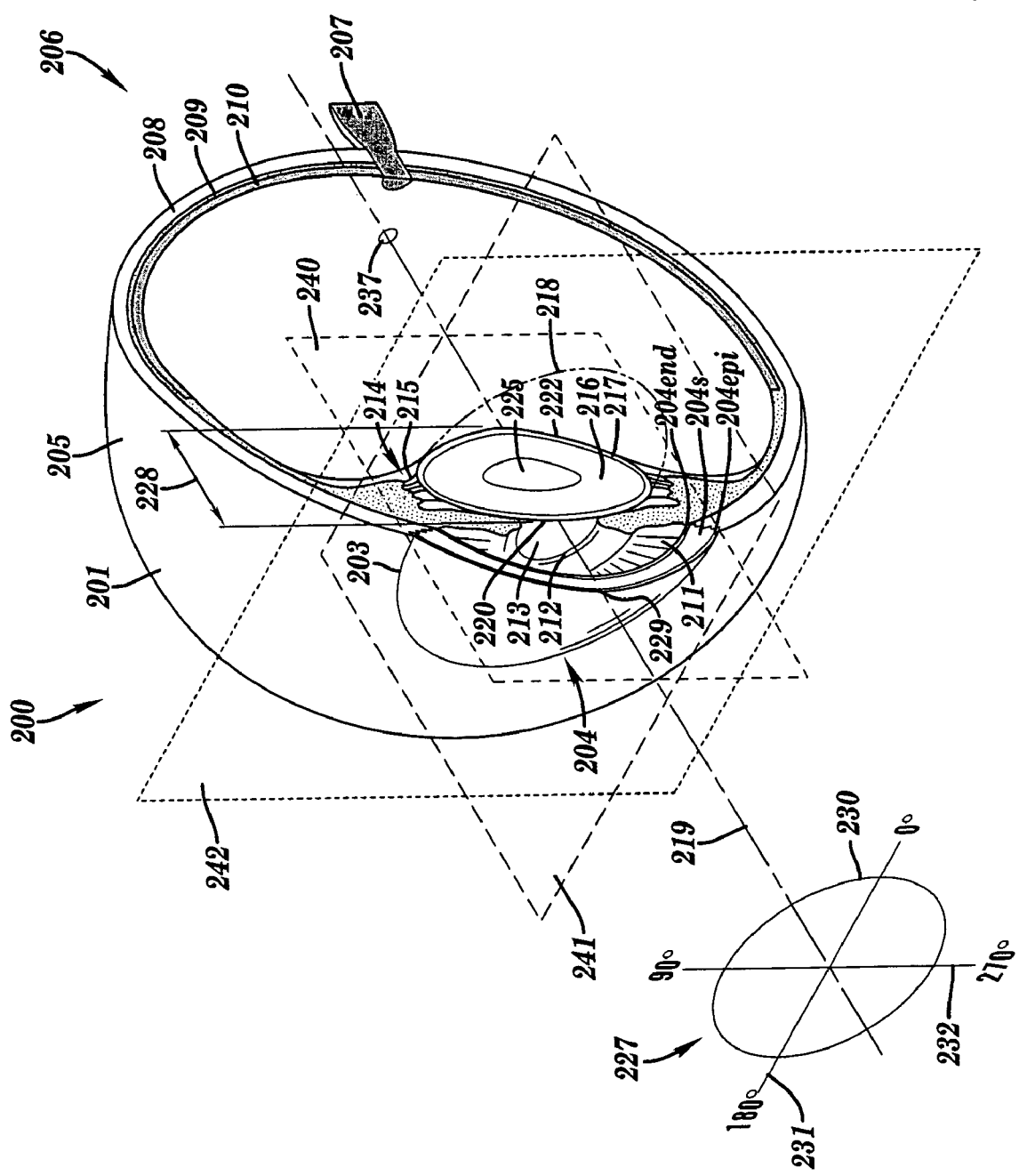
FIG. 1A is a schematic perspective illustration of a human eye.

FIG. 1A is a schematic perspective illustration of a human eye 200, set against an anatomical sagittal plane 240, an anatomical axial plane 241 and an anatomical coronal plane 242, showing that the three-dimensional geometric shape of the human eye may generally be regarded as formed by the intersection of a first larger sphere 201 with a second smaller sphere (not shown in FIG. 1A), the visible portion of which protrudes from first sphere 201 as the anterior convexity of the eye—the transparent cornea 204. The generally circular line of intersection of these spheres forms the anatomic limbus 203, a line of demarcation that circumscribes cornea 204.

The cornea 204 is the eye's interface with the environment and its principal refractive structure. The cornea 204 is a trilamellar structure, having an anterior epithelium 204*epi*, an interior stroma 204*s*, and a posterior endothelium 204*end*. The anterior-most point of the cornea is the corneal vertex 229. Orientation about cornea 204 is determined by reference to meridians 227 in a plane parallel to coronal plane 242, such as reference plane 230. The meridian crossing from zero degrees to 180 degrees 231 and the meridian crossing from 90 degrees to 270 degrees 232, as shown in FIG. 1A, are called principal meridians.

The larger second sphere 201 of the eye 200 outside of the limbus 203 forms the white shell of the eye 205, whose posterior aspect 206 is entered by the optic nerve 207. The shell of the eye 205 is also a tri-lamellar tissue, having an outermost tectonic layer known as the sclera 208, a middle vascular layer known as the choroid 209, and an innermost photosensitive layer known as the retina 210. The choroid 209 and retina 210 are conjunctively referred to as the uvea. The most discriminatingly photosensitive region of the retina is confined to a region called the macula lutea 237. An imaginary vector emanating from macular lutea 237 anteriorward, approximately perpendicular to coronal plane 242, approximately along sagittal plane 240, and through cornea 204, defines the visual axis 219 of the eye 200.

Projecting radially inward from the shell 205 of the eye 200 circumferentially adjacent the limbus 203 is a circular disk-like diaphragm of tissue known as the iris 211, whose innermost circular border forms the margin 212 of an aperture called the pupil 213. The iris forms the aperture stop of the eye. Anatomically, the term "pupil" refers to either the actual or physical opening of the anatomic iris 211, i.e., the physical opening of the aperture stop formed by the iris 211.

When looking at the anatomical pupil 213, from an external viewpoint directed into eye 200 through the cornea 204, what is seen is a virtual image of the anatomical pupil 213 formed by cornea 204. The anterior, through-the-cornea virtual image is called the "entrance" pupil (not shown in FIG. 1A). When looking at the anatomical pupil 213, from an internal viewpoint directed anteriorward through crystalline lens 216 from behind, what is seen is a virtual image of the anatomical pupil 210 formed by crystalline lens 216. The posterior, through-the-lens image of the anatomic pupil 213 is called the "exit" pupil (not shown in FIG. 1A). The entrance pupil appears anterior to the anatomic pupil 213.

Immediately posterior and continuous with the iris 211 is the muscular ciliary body 214, from which there are circumferentially elaborated a plurality of strands, called zonules 215, projecting radially inward to tether the crystalline lens 216 just posterior to iris 211. Zonules 215 insert onto a lens capsule 217 that envelopes the crystalline lens 216. Zonules 215 insert onto lens capsule 217 along a circle generally coincident with the equator 218 of the crystalline lens 216.

Figure 1B:
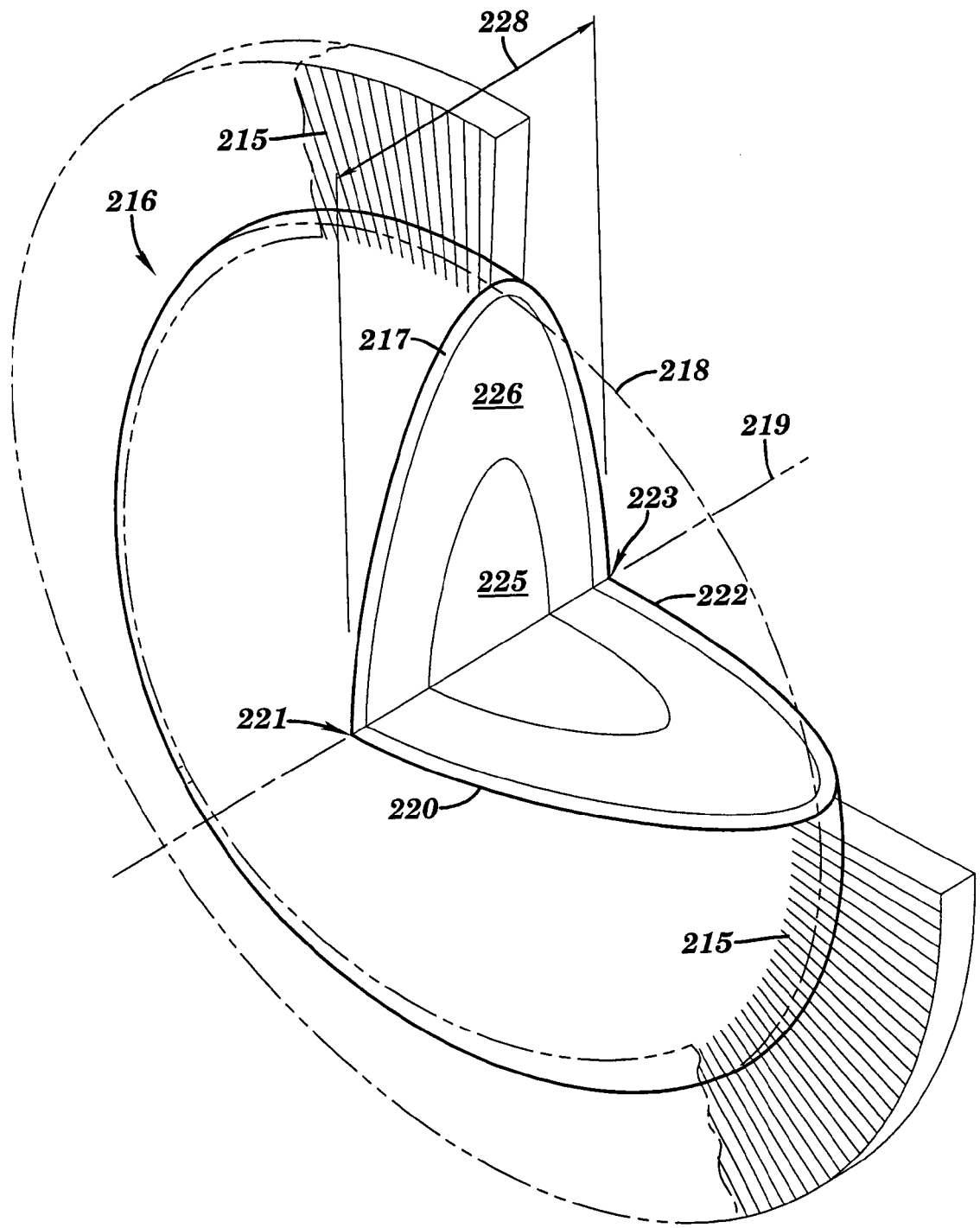
FIG. 1B is a schematic perspective illustration of the crystalline lens and zonular apparatus of a human eye.

As shown in FIG. 1B, in the normal anatomic position, the lens 216 has the general form of an ellipsoid having a principal axis that is oriented horizontally and is generally coincident with the visual axis 219 of the eye 200. The intersection of the visual axis 219 with the anterior surface 220 of the lens capsule 217 defines the anterior pole 221 of the crystalline lens 216; and, the intersection of the visual axis 219 with the posterior surface 222 of the lens capsule 217 defines the posterior pole 223 of the crystalline lens 216. The distance between the anterior pole 221 and the posterior pole 223 along the visual axis 219 defines the antero-posterior diameter 228 of the crystalline lens 216 and determines its antero-posterior thickness. Both the anterior and posterior surfaces, 220 and 222 of the crystalline lens 216 are generally convex, making the crystalline lens 216 a biconvex structure whose posterior convexity is generally steeper (having a smaller radius of curvature) than its anterior convexity.

The lens tissue of lens 216 within the lens capsule 217 is largely comprised of protein-laden cells that endow it with the property of transparency and also endow it with a degree of elasticity. As the crystalline lens 216 ages, the lens tissue within the lens capsule 217 becomes increasingly dense and decreasingly transparent centrally, changes that make it distinguishable into a higher density lens nucleus 225 and a circumscribing lower density lens cortex 226.

Figure 1C:
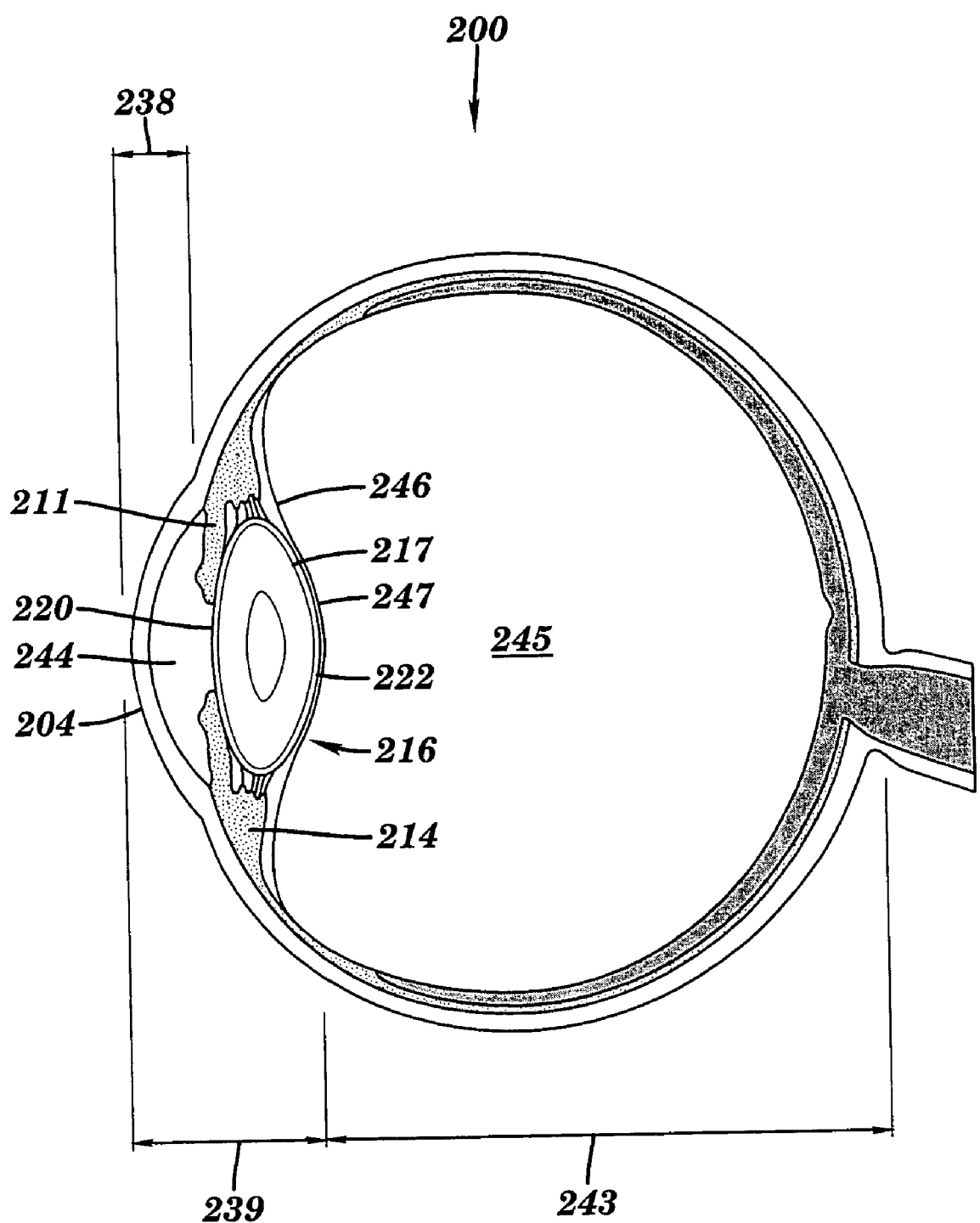
FIG. 1C is a schematic axial cross section of a human eye.

Referring to FIG. 1C in light of FIG. 1A and FIG. 1B, the region of the eye having iris 211 as its base and cornea 204 as a vault or dome is called the anterior chamber 238 of eye 200. The region of eye 200 formed by adding ciliary body 214 and crystalline lens 216 to anterior chamber 238 is called the anterior segment 239 of the eye 200. The remainder of eye 200 is called its posterior segment 243. In the healthy eye, the anterior segment is filled with a thin fluid called the aqueous humor 244 and the posterior segment is filled with a gelatinous liquid called the vitreous humor 245. The anterior surface of the vitreous humor is called the anterior hyaloid membrane 246, in which there is formed a shallow concavity called the anterior hyaloid fossa 247 against which the posterior surface 222 of the lens capsule 217 is apposed.

Both cornea 204 and crystalline lens 216 of eye 200 are endowed with the capacity to refract incoming light arising from an object of regard. In general, cornea 204 has a fixed positive refractive power of about 45 diopters (D). Crystalline lens 216 has a minimum positive refracting power of about 20 D and has an additional variable positive refracting power that slowly declines to near zero with advancing age from a childhood maximum of about 15 D.

The refractive error of an eye is a measure of the degree to which an eye departs from an accepted standard of visual acuity when viewing optotypes or images at a distance of about 6 meters (20 feet) from an examinee. An eye without a refractive error is said to be emmetropic, and a person with emmetropic vision is called an emmetrope. An eye with any refractive error is said to be ametropic, and a person with ametropic vision is called an ametrope. An eye whose refractive error is such that its uncorrected visual acuity in all corneal meridians is superior at 6 m than it is when viewing objects less than 6 m away is said to be (spherically) hyperopic; and, a person with hyperopic vision is called a hyperope. An eye whose refractive error is such its uncorrected visual acuity in all corneal meridians 227 is inferior at 6 m than it is when viewing objects less than 6 m away is said to be (spherically) myopic; and, a person with myopic vision is called a myope. More complex forms of refractive error occur if the uncorrected visual acuity of an eye varies from one corneal meridian to another, in which case the eye is said have an astigmatic refractive error.

Turning next to the subject of accommodation, an object of regard is generally regarded to be distant or "at far" if it is about 6 meters (20 feet) or more away from a subject. An object of regard is generally regarded to be "at near" if it is about ⅓ of a meter (about 14 inches) or closer to a subject. As indicated, supra., accommodation generally refers to the processes by which the lenses of the eyes adapt to maintain an object of regard in sharp focus as it comes increasingly near to the eyes from an initially distant disposition.

Accommodation generally involves two known changes: a change in the refractive state of the eyes and a convergent change, i.e., a change in the angle that the visual axes of the eyes make with respect to one another in a horizontal plane. The refractive change of accommodation is mediated by the crystalline lenses 216 (FIG. 1A, FIG. 1B, FIG. 1C) of both eyes, which increase the convexity of their anterior and posterior surfaces 220 and 222 (FIG. 1A, FIG. 1B, FIG. 1C) and elongate their antero-posterior thicknesses 228 (FIG. 1B), thereby increasing their refractive plus power.

When the eyes of a person regard an object at far, they are said to be in a state of relaxed accommodation. The state of relaxed accommodation does not imply a state of disaccommodation. On the contrary, some tonic accommodation may be present. This is particularly true of refractively uncorrected hyperopes who may unconsciously enlist varying amounts of accommodative plus power at far to neutralize their hyperopia. As used herein, the state of disaccommodation refers to the minimal refractive plus power of the crystalline lens that is present when all accommodation has been eliminated by use of a cycloplegic pharmacologic agent.

When the eyes of a person regard an object at near they are said to be in a state of accommodation, the degree of which generally depends on the proximity of the object of regard to the eyes, with greater degrees of accommodation being invoked by the eyes as the object comes closer to them, until a limiting state of a person's maximum accommodation—a person's accommodative amplitude—has been reached.

In the state of relaxed accommodation, muscles of ciliary body 214 (FIG. 1A), to which zonules 215 (FIG. 1A) are connected, are in a state of relative relaxation, zonules 215 (FIG. 1A) are taut, and crystalline lens 216 (FIG. 1A), upon whose lens capsule 217 (FIG. 1A) zonules 215 (FIG. 1A)

insert, is maintained at its narrowest antero-posterior diameter 228 (FIG. 1A), a state consistent with the shallowest convexity of its anterior and posterior surfaces, 220 and 222 (FIG. 1A), and lower refractive plus power.

In states of accommodation, muscles of the ciliary body 214 (FIG. 1A), to which zonules 215 (FIG. 1A) are connected, are in states of relative contraction, zonules 215 (FIG. 1A) are correspondingly relatively more slack, and crystalline lens 216 (FIG. 1A), upon whose lens capsule 217 (FIG. 1A) zonules 215 (FIG. 1A) insert, is maintained with its antero-posterior diameter 228 (FIG. 1A) increased and the convexity of its anterior and posterior surfaces 220 and 222 (FIG. 1A) increased. In states of accommodation, the refractive plus power of crystalline lens 216 (FIG. 1A) increases to converge divergent light, emanating from an object of regard at near, to a point of sharp focus upon the retina 210.

When the gaze of the eyes falls upon an object that is about 6 meters (20 feet) or more from the eyes, the rays of light arising from the object of regard are generally parallel to one another upon reaching the eyes and, in an emmetrope, the combined plus refractive power of cornea 204 (FIG. 1A) and crystalline lens 216 (FIG. 1A) will converge the parallel rays of light to a point of sharp focus upon retina 210 (FIG. 1A). The distant point at which an object of regard invokes a state of relaxed accommodation in a person is called the person's far point.

When the gaze of the eyes falls upon an object that is at or less than about ⅓ m (14 inches) from the eyes, the rays of light arising from the object of regard are generally divergent to one another upon reaching the eyes and, in an emmetrope, the combined plus power of cornea 204 (FIG. 1A) and crystalline lens 216 (FIG. 1A) must be augmented by the accommodation of crystalline lens 216 (FIG. 1A), so that the divergent rays of light are clearly focused to a point upon retina 210 (FIG. 1A).

The point at which an object of regard invokes the eyes' maximum accommodation in a person is called the person's near point. As indicated, supra., the maximum accommodation that may be invoked by a person's eyes is called the person's accommodative amplitude. The accommodative amplitude, measured in diopters, is simply the reciprocal of the person's near point, measured in meters from the person's eyes. Accommodative amplitude diminishes with age in the approximate manner shown in Table 1.

TABLE 1

Approximate Accommodative Amplitude Associated with Age

| Age | Accommodative Amplitude (D) |
| --- | --- |
| 8 | 14 |
| 25 | 10 |
| 35 | 7 |
| 45 | 4 |
| 55 | 1 |

As used herein, the term dynamic accommodation refers to the intercurrent, time-dependent processes that transform an eye back and forth between any first state of accommodation to any second state of accommodation, which first and second states of accommodation are selectable from a range of accommodation defined by and inclusive of the state of disaccommodation and the state of accommodation corresponding to the accommodative amplitude of the eye.

Accompanying the refractive changes characteristic of accommodation is a nasal-ward (medial) rotation (version) of the eyes in a horizontal plane that makes the visual axes of the eyes, which are essentially parallel in distant vision, convergent in near vision. This nasal-ward rotation is called accommodative convergence.

The concurrent refractive and rotational changes that characterize accommodation are generally symmetrically bilateral phenomena. However, accommodation may be stimulated unilaterally. In this case, the eye that is being stimulated to accommodate—the fixating eye—will provoke a symmetric refractive change in the lens of the contralateral, nonfixating eye. When unilateral stimulation causes the fixating eye to accommodate, the concurrent displacement of the visual axes of the eyes by accommodative convergence is effected entirely by the contralateral, nonfixating eye. That is, the visual system will accept the necessary convergent movement that must accompany the refractive change occurring in the lenses of the eyes during accommodation, as either the sum of two smaller nasal-ward rotations of both eyes or as an equivalent larger nasal-ward rotation of only one eye.

As a human being ages, the crystalline lens increases in volume with concomitant increases in anterior and posterior convexity. Additionally, its capacity to change its shape so as to further increase its anterior and posterior convexity and corresponding refractive plus power, i.e., its accommodative capacity, undergoes a corresponding decline. The point at which the accommodative capacity of the lens begins to fail marks the beginning of a period requiring "reading glasses" of increasing plus power in order to achieve clear focus at near. The condition of failing vision at near is called presbyopia.

Figure 2:
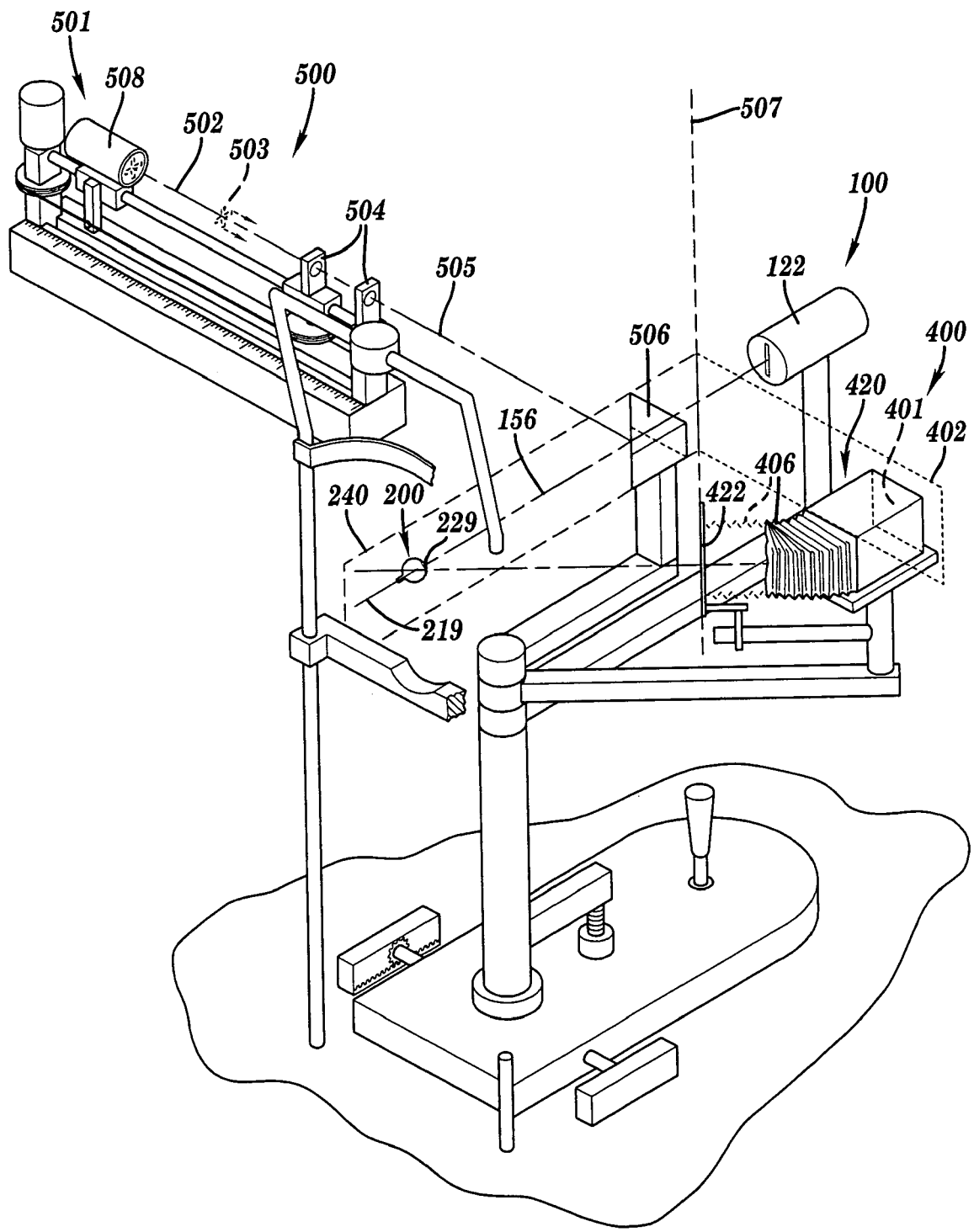
FIG. 2 is a schematic perspective illustration of a first nonlimiting exemplary embodiment of the invention.

FIG. 2 shows a first nonlimiting embodiment of the present invention. The first embodiment is an apparatus comprising an accommodative stimulation device 500, an electromagnetic wave exposure device 100, such as, for example, slit-beam projection lamp 122 emitting slit beam 156, and an imaging device 400, such as, for example, a Scheimpflug videography system 420. The invention acquires imaging information about eye 200 by means of slit-beam projection lamp 122 and Scheimpflug videography system 420, as accommodative stimulation device 500 simultaneously stimulates eye 200 to undergo at least one reversible accommodative transition from any first state of accommodation to any second state of accommodation. The first and second states of accommodation are selectable from a range of accommodation defined by and inclusive of the state of disaccommodation and a state of accommodation corresponding to the accommodative amplitude of eye 200.

Accommodative stimulation device 500 has an axis of projection 502 that is substantially perpendicular to visual axis 219 of eye 200, along which axis of projection 502 an adjustable accommodative target 503 is projected through a system of Badal optics 504, having a Badal optical axis 505, coincident with axis of projection 502, to strike a half-silvered mirror 506 lying in a mirror plane 507 that forms an angle of about 45 degrees with axis of projection 502 and visual axis 219 of eye 200.

The stimulus to accommodation provided by accommodative stimulation device 500 simultaneously triggers dynamic imaging, by operationally coupled imaging device 400, of anterior segment 238 (FIG. 1C) of eye 200, in general, and of crystalline lens 216 (FIG. 1B), lens capsule 217 (FIG. 1B), zonules 215 (FIG. 1B), ciliary body 214 (FIG. 1A), and anterior hyaloid membrane 246 (FIG. 1C) of eye 200, in particular, which imaging continues as eye 200 is stimulated by accommodative stimulation device 500 to undergo one or more predetermined dynamic accommodative transitions.

Figure 3:
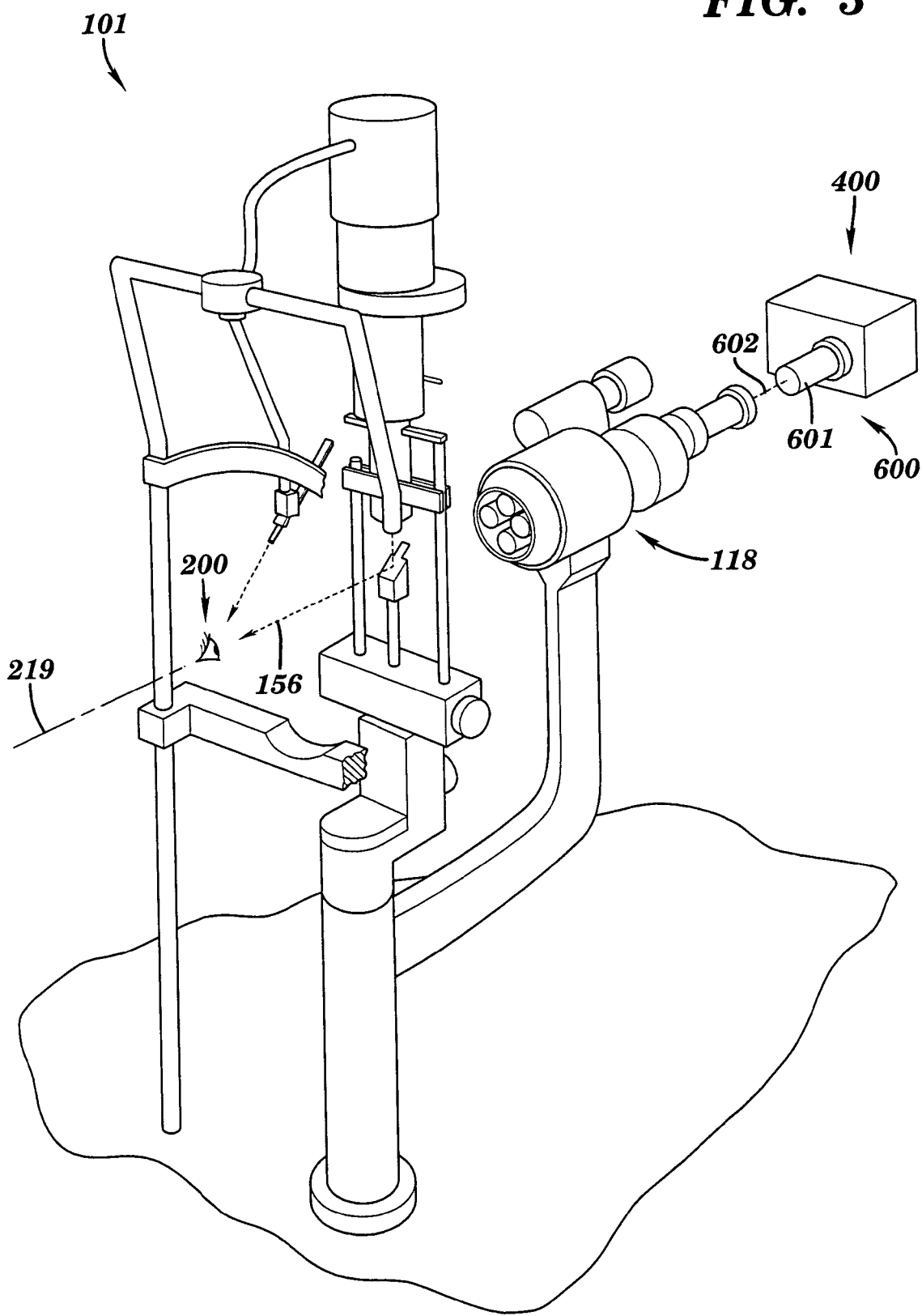
FIG. 3 is a simplified schematic illustration of a slit lamp biomicroscope adapted to perform conventional ophthalmic imaging.

As shown in FIG. 3, conventional imaging of eye 200 typically uses a slit lamp biomicroscope 101 with an imaging device 400 such as, for example, a conventional still film macrophotography camera 600, effectively directed through optics of biomicroscope 118, and having a conventional imaging lens system 601 with a conventional imaging lens axis 602 that is substantially aligned with visual axis 219 of eye 200.

Slit beam 156 is used to illuminate structures on or within eye 200, and is generally oriented to make an angle with visual axis 219 in a horizontal plane ranging between about 20 degrees and 80degrees. The object planes available for sharp focusing in conventional imaging of eye 200, i.e., the planes containing an object on or within eye 200 that may be clearly imaged by conventional still film macrophotography camera 600, generally comprise planes other than anatomical sagittal plane 240 shown in FIG. 2 and in FIG. 1A.

Figure 4:
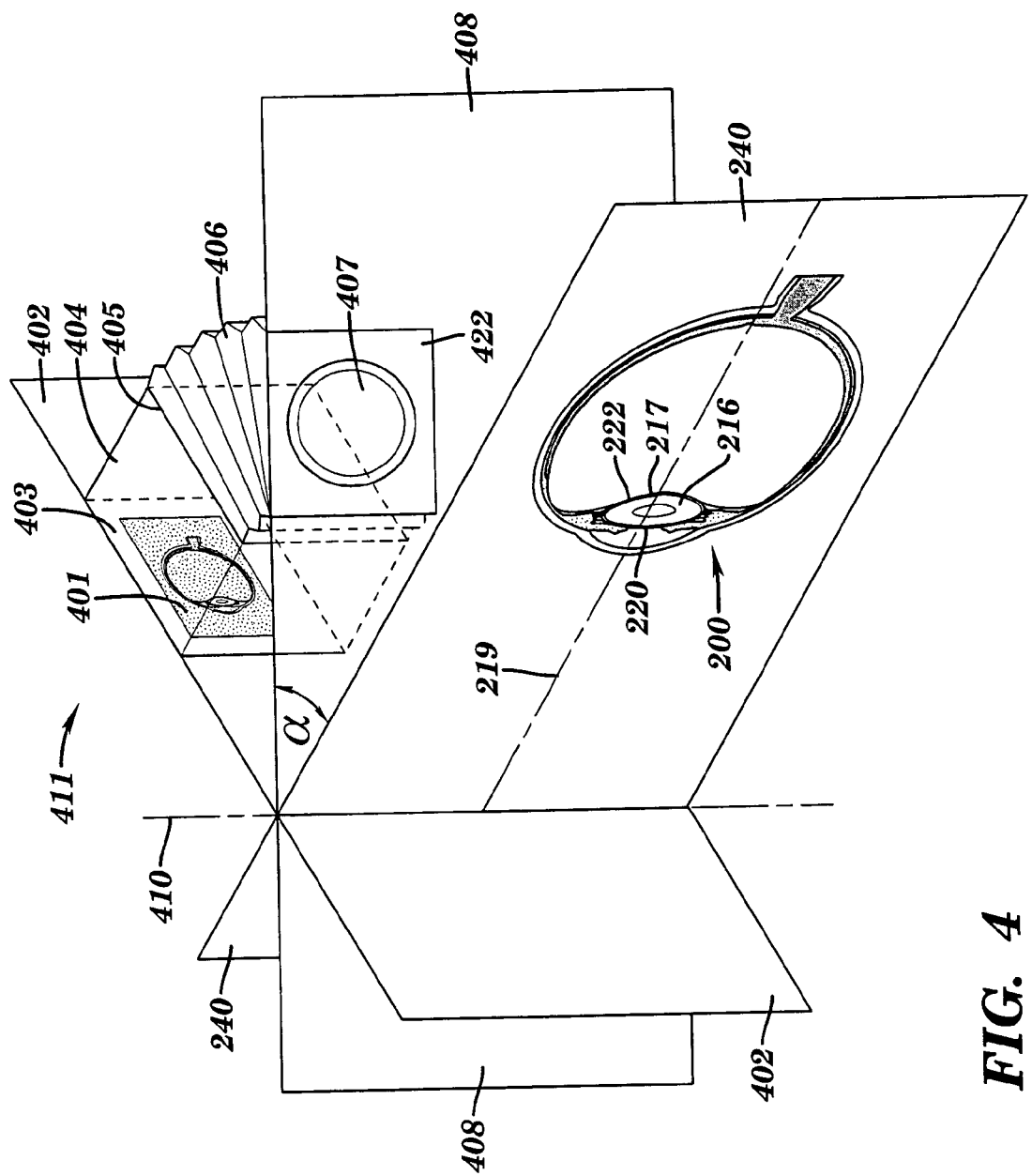
FIG. 4 is a schematic illustration of the principle of Scheimpflug imaging.

As shown in FIG. 4, unlike conventional imaging of eye 200, Scheimpflug imaging of eye 200 is a technique that uniquely enables imaging of structures of eye 200, including crystalline lens 216, in anatomic sagittal plane 240, extending from anterior surface 220 of lens capsule 217 to posterior surface 222 of lens capsule 217. The unique advantage of Scheimpflug imaging over conventional imaging of the eye 200 is that images of, about, and within crystalline lens 216 along visual axis 219 of eye 200 within sagittal plane 240 can be captured.

In FIG. 4, Scheimpflug imaging device 411 has a Scheimpflug imaging medium 401 such as, for example, still or motion picture film, or a still or motion picture digital medium such as, for example a CCD array, oriented with its imaging surface defining a Scheimpflug imaging plane 402 that is generally coincident with back surface 403 of Scheimpflug imaging device body 404. Scheimpflug imaging device body 404 generally has the shape of a rectangular parallelepiped, whose front surface 405 opens onto bellows 406. Bellows 406 terminates in lens housing 422, supporting Scheimpflug imaging lens system 407, shown for the sake of simplicity as a single lens in FIG. 4, defining Scheimpflug imaging lens plane 408.

In FIG. 4, eye 200 is shown schematically in an anatomic sagittal view. Sagittal plane 240 contains visual axis 219 and intersects anterior surface 220 of lens capsule 217 and posterior surface 222 of lens capsule 217. In accordance with the Scheimpflug Principle, in order for an object, such as cross-sectional image of crystalline lens 216 lying in sagittal plane 240, to be sharply focused as a corresponding image on Scheimpflug imaging medium 401, lying in Scheimpflug imaging plane 402, Scheimpflug imaging plane 402, Scheimpflug imaging lens plane 408 and sagittal plane 240 must intersect at common line of intersection 410. In the particular case in which Scheimpflug imaging plane 402 and sagittal plane 240 intersect at common line 410 to form an approximate right angle, that is approximately halved by Scheimpflug imaging lens plane 408, a 1:1 image to object ratio is also achieved.

The Scheimpflug Principle determines the degree to which Scheimpflug lens plane 408 of exemplary Scheimpflug imaging device 411 must be rotated (tilted) away from its conventional parallel orientation to Scheimpflug imaging plane 402 of exemplary Scheimpflug imaging device 411 in order to sharply focus on Scheimpflug imaging plane 402 an object lying in an object plane, i.e., anatomical sagittal plane 240, that is not parallel to Scheimpflug imaging plane 402.

In the present invention angle α, formed by the intersection of Scheimpflug imaging lens plane 408 and anatomical sagittal plane 240 when both planes also intersect Scheimpflug imaging plane 402 (in satisfaction of the Scheimpflug Principle) is called the Scheimpflug angle.

In the present invention, when Scheimpflug imaging lens plane 408 and anatomical sagittal plane 240 intersect Scheimpflug imaging plane 401, and Scheimpflug imaging lens plane 408 forms angle α with anatomical sagittal plane 240, then Scheimpflug imaging lens plane 408, anatomical sagittal plane 240, and Scheimpflug imaging plane 401 are said to be in Scheimpflug alignment.

When, as shown in FIG. 2, electromagnetic wave exposure device 100 comprises slit-beam projection lamp 122 emitting slit beam 156, whose axis of projection is coincident with visual axis 219 of eye 200, and imaging device 400 comprises Scheimpflug videography system 420, accommodative changes occurring in and about crystalline lens 216 in sagittal plane 240 of eye 200 are dynamically imaged without loss of Scheimpflug alignment owing to accommodative convergence, as explained hereinabove.

Figure 5:
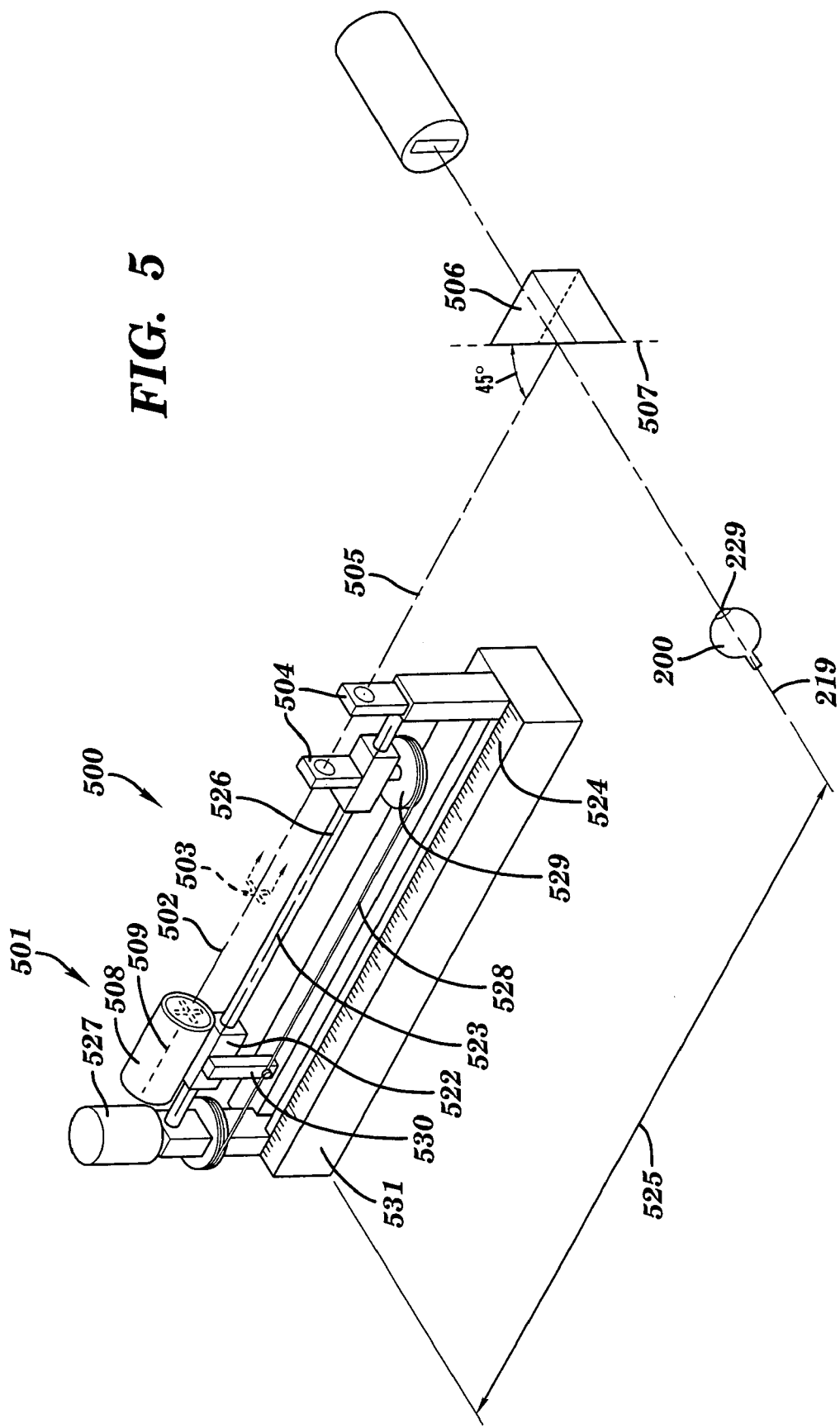
FIG. 5 is a schematic perspective illustration a accommodative stimulation device.

FIG. 5 is a schematic illustration showing a perspective view of accommodative stimulation device 500 common to all embodiments of the present invention. In FIG. 5, accommodative stimulation device 500 comprises a support member 531 supporting an accommodative target projection subsystem 501 having axis of projection 502 that is substantially perpendicular to visual axis 219 of eye 200. Adjustable accommodative target 503 is projected along axis of projection 502 through a multi-lens Badal optical system 504, having a Badal optical axis 505 coincident with axis of projection 502, to strike a half-silvered mirror 506 lying in a mirror plane 507 that forms an angle of about 45 degrees with both axis of projection 502 and visual axis 219 of eye 200.

Accommodative target projection subsystem 501 comprises a projection platform 508 attached to a computer-controlled motorized carriage 522 that is moveable along an axis of travel 523 parallel to a linear scale 524, the limits of which define a Badal space 525. Computer-controlled motorized carriage 522 may be caused to move bidirectionally along axis of travel 523, within Badal space 525, by a suitable driving mechanism, such as, for example, a computer-controlled servo-motor 527 driving a belt 528 that loops about a driving pulley 529, to precisely displace carriage 522 to which belt 528 is operationally attached by a linkage 530.

Alternatively, computer-controlled motorized carriage 522 may be caused to move bidirectionally along axis of travel 523, within Badal space 525, by, for example, a driving engine in the from of an on-board servo-motor that is subject to wireless computer control. The driving mechanism is configured to make computer-controlled motorized carriage 522 moveable between any point in Badal space 525 within a period of time that is substantially less than the minimum response time for accommodation that invokes the accommodative amplitude of eye 200.

Computer-controlled motorized carriage 522 may be constrained to move along axis of travel 523 by, for example, having it ride upon at least one traveling rod 526, as shown in FIG. 5, or, as another example, computer-controlled motorized carriage 522 may be constrained to move along axis of travel 523 by having it engage one or more linear channels or tracks (not shown in FIG. 5), or by being suspended from a monorail or similar rigid pathway (not shown in FIG. 5).

Linear scale 524 is calibrated in diopters of accommodative stimulus, or a substantially equivalent measure of accommodation, provided by projection platform 508 of accommodative target projection subsystem 501 at each position projection platform 508 makes along axis of travel 523. Axis of travel 523 and linear scale 524 are both substantially parallel to axis of projection 502, and both are also substantially perpendicular to visual axis 219 of eye 200.

Multi-lens Badal optical system 504 is effectively disposed so as to place corneal vertex 229 of eye 200 at a distance about equal to the secondary focal length of Badal optical system 504, thereby assuring that:

[i] the degree of accommodation of eye 200 stimulated by adjustable accommodative target 503 is linearly related to the distance of moveable projection platform 508 from Badal optical system 504; and,

[ii] adjustable accommodative target 503 seen by eye 200 does not change size, i.e., the apparent size of adjustable accommodative target 503 perceived by eye 200 will remain constant and be independent of the position of projection platform 508. This feature has the salutary effect of eliminating any changing in size of adjustable accommodative target 503 as a stimulus to accommodation in eye 200.

Figure 6:
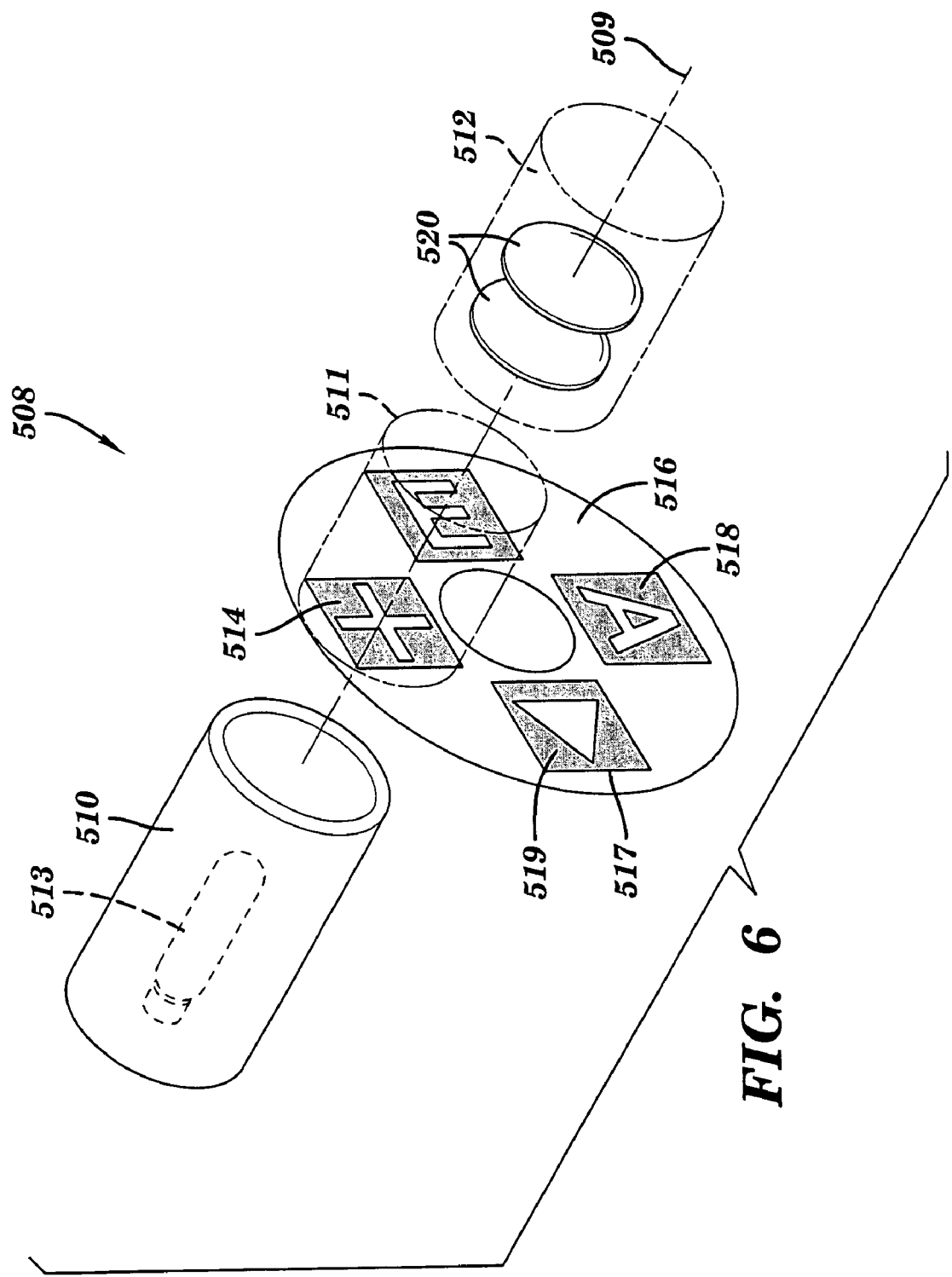
FIG. 6 is a schematic perspective illustration of a set of exchangeable target-image-forming masks.

Projection platform 508 of accommodative target projection subsystem 501 shown in FIG. 5 is shown in greater detail in FIG. 6. In FIG. 6, projection platform 508 is shown in an exemplary hollow cylindrical conformation. Projection platform 508 has a central longitudinal axis 509, an illuminating segment 510, an internal segment 511, and a projecting segment 512. Central longitudinal axis 509 of projection platform 508 defines axis of projection 502 (FIG. 2 and FIG. 5).

Illuminating segment 510 of projection platform 508 is adapted to receive an energizeable source of light 513 outputting light of adjustable intensity. Internal segment 511 of projection platform 508 is adapted to receive at least one member of a set of exchangeable target-image-forming stencils, such as, for example, target-image-forming stencil 514, that may, for example, be arrayed circumferentially along a disk 516, having multiple apertures 517 adapted to accept a variety of stencils forming, for example, accommodative optotypes, such as accommodative optotype 518, or a variety of stencils forming, for example, accommodative figurative target-images, such as accommodative figurative target-image 519, as shown in FIG. 5. Alternatively, exchangeable target-image-forming stencils 514 may, for example, be arrayed linearly along a rectangular strip (not shown in FIG. 5) having multiple apertures adapted to accept a variety of stencils forming accommodative optotypes or figurative target-images.

Projecting segment 512 of projection platform 508 is adapted to house a system of adjustable lenses 520, to correct any refractive error of eye 200, and to transmit light passed by target-image-forming stencil 514 from light source 513 through Badal optical system 504 and thence onto half-silvered mirror 506 (FIG. 5 and FIG. 2).

Figure 7:
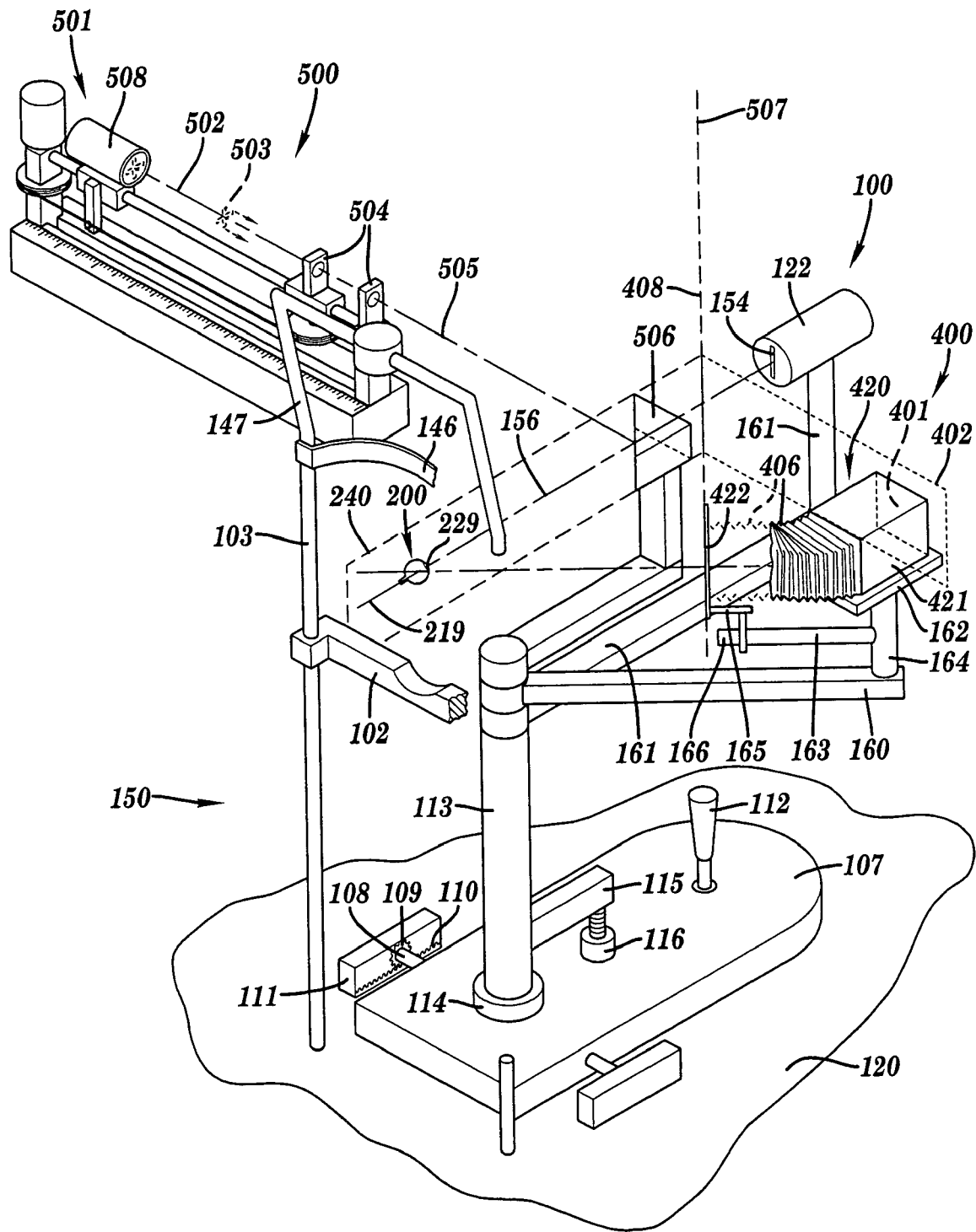
FIG. 7 is a more detailed schematic perspective illustration of a first nonlimiting exemplary embodiment of the invention.

FIG. 7 shows first nonlimiting exemplary embodiment of the invention is greater detail. In FIG. 7, accommodative stimulation device 500 is operationally coupled to a modified slit lamp assembly 150, so that when an examinee's gaze is properly oriented, visual axis 219 of eye 200 is perpendicular to axis of projection 502, and corneal vertex 229 of eye 200 is effectively disposed at a distance equal to the secondary focal length of Badal optical system 504 of accommodative target projection subsystem 501. Projection platform 508 of accommodative target projection subsystem 501 is in the form of a generally cylindrical hollow projection tube.

Modified slit lamp assembly 150 as incorporated into first nonlimiting exemplary embodiment of the invention includes a head rest frame 147 mounted on a table 120 or other suitable support. Head rest frame 147 has a vertically adjustable chin support 102 extending horizontally between paired, parallel, upright, telescoping columns 103, thereby raising or lowering visual axis 219 of eye 200 to the level of a slit beam 156. An examinee's forehead is supported by forehead band 146.

A carriage 107 is mounted to be movable along table 120 relative to head rest frame 147 by means of a spherical element (not shown in FIG. 7) mounted in carriage 107 and riding on the surface of table 120, carriage 107 being laterally slidable along a shaft 108 having pinions 109 at its ends engageabley riding on parallel racks 110 formed in housings 111 mounted on surface of table 120. A joystick 112 extends from carriage 107 to be moved by an examiner to provide anterior and posterior movement of carriage 107 along parallel racks 110 and left-right lateral movement of carriage 107 along shaft 108.

Mounted on carriage 107 is a pivot assembly 113 comprising a hub 114 having an arm 115 extending transversely therefrom and cooperating with a vertical adjustment knob 116 for raising and lowering pivot assembly 113. Pivot assembly 113 includes imaging device arm 160 carrying a Scheimpflug Videography System 420 on a horizontally rotatable first platform 162 supported by a vertical column 164 pivotably mounted on the terminus of imaging device arm 160. A horizontal stalk 163 rotatably inserts into a vertical column 164 and extends from vertical column 164 to support a horizontally rotatable second platform 165 at free end 166 of horizontal stalk 163.

Pivot assembly 113 also includes an L-shaped slit-beam illumination arm 161 carrying a horizontally oriented slit beam projection lamp 122. Imaging device arm 160 and L-shaped slit-beam illumination arm 161 are pivotally mounted on a common vertical pivot pin (not shown in FIG. 7), supported by hub 114 and pivot assembly 113, such that Scheimpflug videography system 420 and slit beam projection lamp 122 are concentrically horizontally pivotal about a common vertical axis defined by columnar pivot assembly 113.

Scheimpflug Videography System 420, mounted on horizontally rotatable first platform 162, comprises a video imaging device 421, such as, for example, a high resolution (1024 by 1024 pixel) Dalsa D4 digital camera, coupled to a bellows 406 that opens into a lens housing 422, carried by horizontally rotatable second platform 165, for support of an imaging lens (not shown in FIG. 7), such as for, example, a Nikon Nikkor Macro Lens with an objective of 1.75:1.

Image device arm 160, horizontally rotatable first platform 162 carrying video imaging device 421, horizontal stalk 163, and horizontally rotatable second platform 165 carrying lens housing 422 are independently adjustable to enable the imaging lens (not shown in FIG. 7) that is supported by lens housing 422 in imaging lens plane 408, to be horizontally rotated with respect to imaging plane 402 and sagittal plane 240 to provide a Scheimpflug alignment of these planes.

Slit beam projection lamp 122 has a variable intensity lamp (not shown in FIG. 7) arranged to direct light through an internal adjustable slit optical system (not shown in FIG. 7) comprising lenses, filters, diaphragms and apertures, whose arrangement fashions light emitted from the variable intensity lamp into slit beam 156, having variable height and width, that is directed through slit aperture 154 of slit beam projection lamp 122 to arrive at eye 200 directed along a slit beam axis substantially coincident with visual axis 219 of eye 200. Slit aperture 154 can be rotated to vertically or horizontally orient slit beam 156.

When slit beam 156 is directed into eye 200, as shown in FIG. 1C, it sequentially intercepts, from anterior to posterior, the cornea 204, the aqueous humor 244, the anterior surface 220 of the lens capsule 217, the crystalline lens 216, the posterior surface 222 of the lens capsule 217, the anterior hyaloid membrane 246 and the anterior aspect of vitreous humor 245, all shown in FIG. 1C.

If slit beam 156 is directed into the anterior aspect of eye 200 so as to make an angle with visual axis 219 of eye 200 that is greater than or equal to zero degrees but less than ninety degrees, it will illuminate the foregoing tissues, rendering them visible in the plane that the slit beam forms as it intersects each tissue.

When using first embodiment of the invention, an examinee's head is supported by a headrest frame 147 having a vertically adjustable chin support 102 and a forehead rest 146 so that the examinee's head is not allowed to move. Thereafter, an examiner adjusts parallel upright telescoping columns 103 to move chin support 102 up and down, thereby bringing eye 200 into a desired examining position. The orientation of the visual axis 219 of eye 200 may be maintained during imaging of dymamic accommodation by instructing an examinee to maintain his or her gaze at adjustable accommodative target 503 reflected onto visual axis 219 by half-silvered mirror 506 disposed in mirrror plane 507.

By operationally coupling modified slit lamp assembly 150 with Scheimpflug videography system 421 to accommodative stimulation device 500, imaging information accompanying dynamic accommodation may be captured to yield valuable information about the optics of accommodation that may, inter alia, be useful in the development and perfection of intraocular lenses having the capacity to emulate dynamic accommodation. Furthermore, by operationally coupling modified slit lamp assembly 150 with Scheimpflug videography system 421 to accommodative stimulation device 500, imaging information regarding refractive errors that accompany presbyopia, cataractogenesis and other crystalline lens pathological conditions may be captured.

Figure 8:
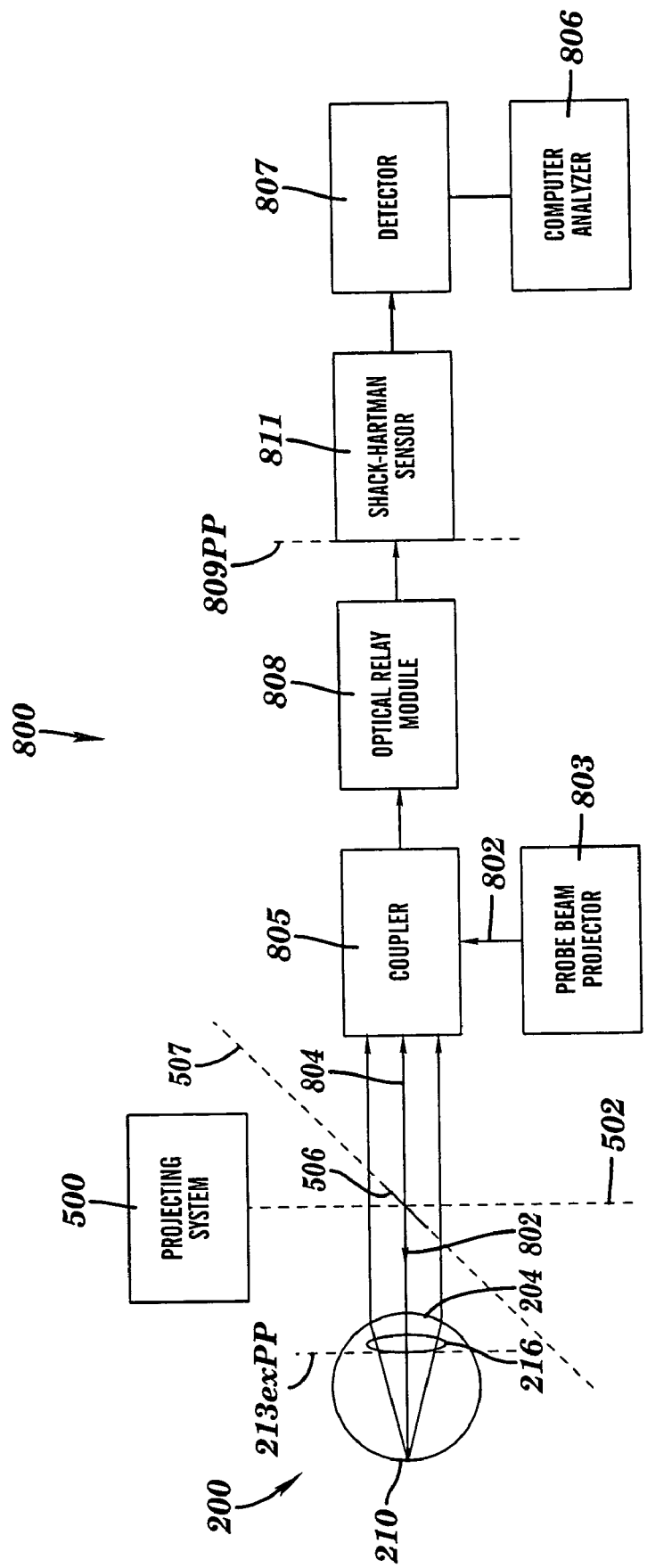
FIG. 8 is a block diagram of a second nonlimiting exemplary embodiment of the invention.

A second nonlimiting exemplary embodiment of the invention is shown in FIG. 8, a schematic illustration in which accommodative stimulation device 500 is interfaced with an exemplary wavefront aberrometer 800 that measures optical aberrations of eye 200. Exemplary wavefront aberrometer utilizes a Shack-Hartmann sensor 811. A source beam 802 of infrared or near infrared radiation emitted from a beam projector 803, such as, for example, an infrared laser or light emitting diode, is projected, via an optical coupler 805 onto retina 210 of eye 200 through cornea 204 and crystalline lens 216. Efferent beam 804 of radiation is then reflected and scattered from retina 210 back through crystalline lens 216, cornea 204, appearing to emerge from an exit pupil (not shown in FIG. 8) in exit pupillary plane 213exPP, and carrying information relating to optical aberrations of eye 200 such as, for example, chromatic aberrations, spherical aberrations, lenticular aberrations, monochomatic aberrations, and, in principle, dynamic accommodative aberrations If, for example, eye 200 is emmetropic, without aberrational error, the wavefront profile of efferent beam 804 at exit pupillary plane 213exPP is planar. For a myopic or hyperopic eye without aberrational error, the wavefront profile of efferent beam 804 at exit pupillary plane 213exPP is spherical. For an eye with aberrational errors, the wavefront profile of efferent beam 804 at exit pupil plane 213exPP is irregularly distorted. Wavefront aberrometer 801 measures the wavefront profile of efferent beam 804 at exit pupil plane 213exPP to determine optical aberrations that comprise higher order refractive errors of eye 200.

The wavefront of efferent beam 804 at exit pupil plane 213exPP passes through half-silvered mirror 506 of accommodative stimulation device 500, disposed in mirror plane 507 oriented at 45 degrees to projection axis 502, and optical coupler 805, to optical relay module 808. Optical relay module 808 relays the wavefront of efferent beam 804 from exit pupillary plane 213exPP of eye 200 to conjugate plane 809PP at Shack-Hartmann sensor 811.

Shack-Hartmann sensor 811 comprises a lenslet array (not shown in FIG. 8) that is disposed at plane 809PP conjugate to exit pupillary plane 213exPP. The lenslet array passes efferent beam 804 into lenslet sub-apertures (not shown in FIG. 8), and forms a Shack-Hartmann spot pattern (not shown in FIG. 8) at a focal plane of the lenslet array. The Shack-Hartmann spot pattern carries optical aberrational information of the wavefront profile of efferent beam 804. Detector 807 detects the Shack-Hartmann spot pattern and outputs a digital signal that is applied as input to a computer analyzer 806. Computer analyzer 806 extracts aberration information from the wavefront profile, and calculates higher order refractive errors of eye 200 in accordance with any one of a number of methods using the digital signal input by detector 807.

By operationally coupling wavefront aberrometer 800 to accommodative stimulation device 500, dynamic higher order refractive errors that accompany dynamic accommodation may be measured to yield valuable information about the optics of accommodation that may, inter alia, be useful in the development and perfection of intraocular lenses having the capacity to emulate dynamic accommodation. Furthermore, by operationally coupling wavefront aberrometer 800 to accommodative stimulation device 500, dynamic higher order refractive errors that accompany presbyopia, cataractogenesis and other crystalline lens pathological conditions may be isolated, quantified and established in mathematically functional relationships.

What is claimed is:

1. An apparatus comprising an accommodative stimulation device, an electromagnetic wave exposure device, and an imaging device, said apparatus acquiring imaging information about an eye by means of said electromagnetic wave exposure device and said imaging device, as said accommodative stimulation device simultaneously stimulates said eye to undergo at least one reversible accommodative transition from any first state of accommodation to any second state of accommodation, said accommodative stimulation device having an axis of projection that is substantially perpendicular to a visual axis of said eye, along which axis of projection an adjustable accommodative target is projected through a system of Badal optics, having a Badal optical axis coincident with said axis of projection, to strike a half-silvered mirror lying in a plane that forms an angle of about 45 degrees with said axis of projection and said visual axis of said eye, wherein said electromagnetic wave exposure device comprises a slit beam of a slit beam projection lamp and said imaging device comprises a Schimpflug videography system.

2. The apparatus of claim 1, wherein said first and second states of accommodation are selectable from a range of accommodation defined by and inclusive of a state of total disaccommodation and a state of accommodation corresponding to the accommodative amplitude of said eye.

3. The apparatus of claim 1, wherein said accommodative stimulation device comprises a projection platform having a central longitudinal axis, an illuminating segment, an internal segment, and a projecting segment, said illuminating segment being adapted to receive a source of light, said central longitudinal axis defining said axis of projection, said internal segment being adapted to receive at least one member of a set of exchangeable target-image-forming masks, toward which light from said source of light is directed, and said projecting segment being adapted to house a system of adjustable lenses for correcting any refractive error of said eye and receiving said light transmitted through said set of exchangeable target-image-forming masks for passage through said system of Badal optics onto said half-silvered mirror, thereby forming said adjustable accommodative target.

4. The accommodative stimulation device of claim 3, wherein said projection platform is attached to a computer-controlled motorized carriage that is moveable along an axis of travel parallel to a linear scale, the limits of which linear scale define a Badal space, said linear scale being calibrated in diopters of accommodative stimulus provided by said projection platform at each position of said projection platform along said axis of travel, said axis of travel and said linear scale being substantially parallel to said axis of projection, said axis of travel and said linear scale further being substantially perpendicular to said visual axis of said eye.

5. The accommodative stimulation device of claim 4, wherein said computer-controlled motorized carriage is moveable between any points within said Badal space within a period of time that is substantially less than a minimum response time for full accommodation in a mammalian eye.

6. The apparatus of claim 1, wherein said electromagnetic wave exposure device comprises an electromagnetic wave emitter of a wavefront aberrometer and said imaging device comprises a wavefront aberrometer.

7. An apparatus comprising an accommodative stimulation device, a slit beam of a slit beam projection lamp projecting a slit beam substantially coincident with an anatomical sagittal plane of an eye and substantially coincident with a visual axis of said eye, and a Scheimpflug videography system having a Scheimpflug imaging plane and a Scheimpflug imaging lens plane that intersect said anatomical sagittal plane in a Scheimpflug alignment, said apparatus acquiring imaging information about said eye by means of said slit beam of said slit beam projection lamp and said Scheimpflug videography system, as said accommodative stimulation device simultaneously stimulates said eye to undergo at least one reversible accommodative transition from any first state of accommodation to any second state of accommodation, without loss of Scheimpflug alignment, said accommodative stimulation device having an axis of projection that is substantially perpendicular to a visual axis of said eye, along which axis of projection an adjustable accommodative target is projected through a system of Badal optics, having a Badal optical axis coincident with said axis of projection, to strike a half-silvered mirror lying in a plane that forms an angle of about 45 degrees with said axis of projection and said visual axis of said eye.

8. The apparatus of claim 7, wherein said first and second states of accommodation are selectable from a range of accommodation defined by and inclusive of a state of total disaccommodation and a state of accommodation corresponding to the accommodative amplitude of said eye.

9. The apparatus of claim 7, wherein said accommodative stimulation device comprises a projection platform having a central longitudinal axis, an illuminating segment, an internal segment, and a projecting segment, said illuminating segment being adapted to receive a source of light, said central longitudinal axis defining said axis of projection, said internal segment being adapted to receive at least one member of a set of exchangeable target-image-forming masks, toward which light from said source of light is directed, and said projecting segment being adapted to house a system of adjustable lenses for correcting any refractive error of said eye and receiving said light transmitted through said set of exchangeable target-image-forming masks for passage through said system of Badal optics onto said half-silvered mirror, thereby forming said adjustable accommodative target.

10. The accommodative stimulation device of claim 9, wherein said projection platform is attached to a computer-controlled motorized carriage that is moveable along an axis of travel parallel to a linear scale, the limits of which linear scale define a Badal space, said linear scale being calibrated in diopters of accommodative stimulus provided by said projection platform at each position of said projection platform along said axis of travel, said axis of travel and said linear scale being substantially parallel to said axis of projection, said axis of travel and said linear scale further being substantially perpendicular to said visual axis of said eye.

11. The accommodative stimulation device of claim 10, wherein said computer-controlled motorized carnage is moveable between any points within said Badal space within a period of time that is substantially less than a minimum response time for full accommodation in a mammalian eye.

12. A method comprising the steps of:

a stimulating an eye to undergo at least one reversible accommodative transition from any first state of accommodation to any second state of accommodation by projecting a light from a light source on an illuminating segment of a projection platform that has an axis of projection and that is attached to a motorized carriage, through at least one member of a set of exchangeable target-image-forming masks on an internal segment of said projection platform, thereafter passing said light through a system of adjustable lenses for correcting any refractive error of said eye onto a system of Badal optics having a Badal optical axis coincident with said axis of projection, said Badal optical axis also being substantially perpendicular to a visual axis of said eye, said light emerging from said system of Badal optics and striking a half-silvered mirror lying in a plane forming an angle of about 45 degrees with said axis of projection and said visual axis, thereby forming an adjustable accommodative target; and, b. adjusting said adjustable accommodative target by moving said motorized carriage along an axis of travel that is parallel to said axis of projection, between any two points within the limits of a parallel linear scale, at a rate that is substantially less than a minimum response time for full accommodation in a mammalian eye, said linear scale being calibrated in diopters of accommodative stimulus provided by said projection platform at each position of said projection platform along said axis of travel, said axis of travel and said linear scale being substantially perpendicular to said visual axis of said eye; and, c. simultaneously acquiring imaging information about said eye by simultaneously exposing said eye to electromagnetic waves and simultaneously imaging said eye during said least one reversible accommodative transition from any first state of accommodation to any second state of accommodation, wherein said step of simultaneously exposing comprises simultaneously illuminating said eye using a slit beam of a slit lamp projection lamp and said step of simultaneously imaging comprises simultaneously videographing said eye using a Scheimpflug videography device.

13. The method of claim 12, wherein said first and second states of accommodation are selectable from a range of accommodation defined by and inclusive of a state of total disaccommodation and a state of accommodation corresponding to the accommodative amplitude of said eye.

14. The method of claim 12, wherein said step of simultaneously exposing comprises simultaneously exposing said eye to the emissions of an electromagnetic wave emitter of a wavefront aberrometer and said step of simultaneously imaging comprises simultaneously profiling said eye using a wavefront aberrometer.

* * * * *